US007865375B2

United States Patent
Lancaster et al.

(10) Patent No.: US 7,865,375 B2
(45) Date of Patent: Jan. 4, 2011

(54) SYSTEM AND METHOD FOR MULTIDIMENSIONAL EXTENSION OF DATABASE INFORMATION USING INFERRED GROUPINGS

(75) Inventors: Brian J. Lancaster, Merriam, KS (US); Michael E. Yarbrough, Lees Summit, MO (US); Kent D. Parkins, Parkville, MO (US); John H. Gragg, Overland Park, KS (US); Douglas S. McNair, Leawood, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

(21) Appl. No.: 11/325,004

(22) Filed: Jan. 3, 2006

(65) Prior Publication Data

US 2007/0005154 A1 Jan. 4, 2007

Related U.S. Application Data

(60) Provisional application No. 60/714,541, filed on Jan. 3, 2005.

(51) Int. Cl.
*G06Q 10/00* (2006.01)
*G06Q 50/00* (2006.01)
*G06Q 40/00* (2006.01)
*A61B 5/00* (2006.01)
*G06F 19/00* (2006.01)

(52) U.S. Cl. ............................................. 705/3; 705/2
(58) Field of Classification Search .................... 705/2, 705/3, 4
See application file for complete search history.

(56) References Cited

U.S. PATENT DOCUMENTS 4,675,147 A 6/1987 Schaefer et al.

(Continued)

OTHER PUBLICATIONS

Office Action mailed Mar. 13, 2007, in U.S. Appl. No. 10/834,229, 12 pp.

(Continued)

*Primary Examiner*—Gerald J. O'Connor
*Assistant Examiner*—Amber Altschul
(74) *Attorney, Agent, or Firm*—Shook, Hardy & Bacon L.L.P.

(57) ABSTRACT

A system and method for receiving medical or other database information and pregrouping and extending that data include a data enhancement layer configured to generate additional stored dimensions capturing the data and relevant attributes. Data sources such as hospitals, laboratories and others may therefore communicate their clinical data to a central warehousing facility which may assemble and extend the resulting aggregated data for data mining purposes. Varying source format and content may be conditioned and conformed to a consistent physical or logical structure. The source data may be extended and recombined into additional related dimensions, pre-associating meaningful attributes for faster querying and storage. The attributes, data and other pieces of information may likewise in embodiments be subjected to an inference analysis to determine whether previously unidentified or unexploited relationships may exist within the universe of source data, for instance using correlation, inference or other analytic techniques. Newly detected, identified or inferred data groupings, which may for instance reveal hidden trends or patterns residing in the data, may then be added back to the enhanced data groupings. Users running analytics against the resulting medical or other datamarts may therefore access a richer set of related information, more powerful sets of predictive models as well as have their queries and other operations run more efficiently.

32 Claims, 8 Drawing Sheets

U.S. PATENT DOCUMENTS

| | | | |
|---|---|---|---|
| 5,664,109 A | 9/1997 | Johnson | |
| 5,831,631 A | 11/1998 | Light | |
| 5,964,700 A * | 10/1999 | Tallman et al. | 600/300 |
| 5,966,139 A * | 10/1999 | Anupam et al. | 345/440 |
| 5,970,464 A * | 10/1999 | Apte et al. | 705/4 |
| 5,991,733 A * | 11/1999 | Aleia et al. | 705/8 |
| 6,073,115 A * | 6/2000 | Marshall | 705/35 |
| 6,163,781 A | 12/2000 | Wess | |
| 6,177,940 B1 | 1/2001 | Bond | |
| 6,211,887 B1 | 4/2001 | Meier | |
| 6,285,377 B1 | 9/2001 | Greenbaum et al. | |
| 6,343,508 B1 | 2/2002 | Feller | |
| 6,401,085 B1 * | 6/2002 | Gershman et al. | 707/4 |
| 6,551,243 B2 * | 4/2003 | Bocionek et al. | 600/300 |
| 6,567,786 B1 * | 5/2003 | Bibelnieks et al. | 705/14 |
| 6,578,003 B1 * | 6/2003 | Camarda et al. | 705/3 |
| 6,584,445 B2 | 6/2003 | Papageorge | |
| 6,669,631 B2 * | 12/2003 | Norris et al. | 600/300 |
| 6,687,685 B1 * | 2/2004 | Sadeghi et al. | 706/15 |
| 6,804,656 B1 | 10/2004 | Rosenfeld | |
| 6,826,578 B2 * | 11/2004 | Brackett et al. | 707/104.1 |
| 6,981,228 B1 | 12/2005 | Chen et al. | |
| 7,002,580 B1 | 2/2006 | Aggala et al. | |
| 2002/0065758 A1 * | 5/2002 | Henley | 705/37 |
| 2003/0088438 A1 | 5/2003 | Maughan et al. | |
| 2003/0093311 A1 * | 5/2003 | Knowlson | 705/10 |
| 2003/0208378 A1 | 11/2003 | Thangaraj et al. | |
| 2003/0212580 A1 | 11/2003 | Shen | |
| 2003/0233031 A1 * | 12/2003 | Rice | 600/300 |
| 2004/0172299 A1 * | 9/2004 | Paul | 705/2 |

OTHER PUBLICATIONS

Office Action mailed Nov. 16, 2007, in U.S. Appl. No. 10/665,560, 13 pp.

Hearst, "Cat-a-Cone: An Interactive Interface for Specifying Searches and Viewing Retrieval results using a Large Category Hierarchy," Jul. 27, 1997. Proceedings of the 20th Annual International ACM SIGIR Conference on Research and Development in Information Retrieval, pp. 246-255.

Spoerri, "InfoCrystal: A Visual Tool for Information Retrieval," Oct. 25, 1993, Visualization '93, Proceedings, IEEE Conference, pp. 11-20.

NOA mailed Dec. 29, 2009, in U.S. Appl. No. 10/665,560, 11 p.

Office Action mailed Jun. 9, 2009, in U.S. Appl. No. 10/665,560, 7 pp.

Final Office Action mailed Oct. 13, 2009, in U.S. Appl. No. 10/665,560, 13 pp.

Office Action mailed Aug. 5, 2008, in U.S. Appl. No. 10/720,086, 10 pp.

Final Office Action mailed Mar. 3, 2009, in U.S. Appl. No. 10/720,086, 12 pp.

Office Action mailed Nov. 9, 2009, in U.S. Appl. No. 10/720,086, 11 pp.

Final Office Action mailed Apr. 27, 2010, in U.S. Appl. No. 10/720,086, 13 pp.

Office Action, mailed Oct. 26, 2010, in U.S. Appl. No. 10/720,086, 19 pp.

* cited by examiner

SYSTEM AND METHOD FOR MULTIDIMENSIONAL EXTENSION OF DATABASE INFORMATION USING INFERRED GROUPINGS

CROSS-REFERENCE TO RELATED APPLICATIONS

This application claims the benefit of U.S. Provisional Application No. 60/714,541, filed Jan. 3, 2005 (originally filed as a nonprovisional application and granted U.S. application Ser. No. 11/025,995; Petition to Convert Nonprovisional application to Provisional Application under 37 C.F.R. §1.53(c)(2) filed Nov. 3, 2005), which is hereby incorporated by reference as if set forth in its entirety herein. Additionally, the subject matter of this application is related to the subject matter of U.S. Provisional Patent Application Ser. No. 60/498,283 filed Aug. 28, 2003 entitled "System and Method for Multidimensional Extension of Database Information"; to the subject matter of U.S. patent application Ser. No. 10/665,560 filed Sep. 22, 2003 entitled "System and Method for Multidimensional Extension of Database Information", which application is a utility application converted from U.S. Provisional Patent Application Ser. No. 60/498,283; to the subject matter of U.S. Provisional Patent Application Ser. No. 60/508,273 filed Oct. 6, 2003 entitled "System and Method for Management Interface for Clinical Environments"; to the subject matter of U.S. patent application Ser. No. 10/720,086 filed Nov. 25, 2003 entitled "System and Method for Evidence-Based Modeling of Clinical Operations"; and to the subject matter of U.S. patent application Ser. No. 10/834,229 filed Apr. 29, 2004, entitled "System and Method for Management Interface for Clinical Environments", which application is a utility application converted from U.S. Provisional Patent Application Ser. No. 60/508,273; each of which applications is assigned or under obligation of assignment to the same entity as this application, and each of which applications is hereby incorporated by reference.

FIELD OF THE INVENTION

The invention relates to the field of information technology, and more particularly to techniques for generating inferred groupings to enhance large-scale, multidimensional medical or other data to permit more efficient data mining, prediction and other operations, such as on a clinical or other database.

BACKGROUND OF THE INVENTION

The advent of powerful servers, large-scale data storage and other information infrastructure has spurred the development of advanced data warehousing and data mining applications. Standard query language (SQL) engines, on-line analytical processing (OLAP) databases and inexpensive large disk arrays have for instance been harnessed in financial, scientific, medical and other fields to capture and analyze vast streams of transactional, experimental and other data. The mining of that data can reveal sales trends, weather patterns, disease epidemiology and other patterns not evident from more limited or smaller-scale analysis.

In the case of medical data management, the task of receiving, conditioning and analyzing large quantities of clinical information is particularly challenging. The sources of medical data, for instance, may include diverse or various independent hospitals, laboratories, research or other facilities, each of which may generate data records at different times and in widely varying formats. Those various data records may be pre-sorted or pre-processed to include different relationships between different fields of that data, based upon different assumptions or database requirements. When received in a large-scale data warehouse, the aggregation of all such differing data points may be difficult to store in a physically or logically consistent structure. Data records may for instance contain different numbers or types of fields, which may have to be conformed to a standard format for warehousing and searching.

Even when conditioned and stored, that aggregation of clinical data may prove difficult to analyze or mine for the most clinically relevant or other data, such as those indicating a disease outbreak or adverse reactions to drugs or other treatments. That is in part because the data ultimately stored or accessed for reports may only contain or permit relationships between various parts of the data which are defined at either the beginning or end of the data management process. That is, the data may reflect only those relationships between different fields or other portions of the data which are defined and embedded by or in the original data source, or which an end user explicitly requests in a query for purposes of generating a report.

Relying on source-grouped data is a rigid approach which may neglect or omit desired relationships, while relying on manual or back-end queries may tax the OLAP or other query engine being used, and in any event may change the fundamental limitations of the data store and searchable structures. Moreover, in the case of moderate to larger-scale clinical data marts, thousands of variables, dimensions, attributes and other objects may obscure potentially useful clinical relationships in the complex of data. If those relationships are not defined by original data structures or probed by individual queries or reports, the information encoded in those correlations may never come to light. Those types of undiscovered relationships may represent lost clinical or operational opportunities, such as detection of promising treatment regimes or potential cost savings in a given service line. Other challenges in receiving, storing and analyzing large-scale medical and other data exist.

SUMMARY OF THE INVENTION

The invention overcoming these and other problems in the art relates in one regard to a system and method for multidimensional extension of database information using inferred groupings, in which one or more data sources may communicate clinical or other data to network resources including a data enhancement layer before ultimate storage in a data warehouse or other storage facility. The data enhancement layer along with associated components may prepare and extend the constituent data sets into logical structures reflecting meaningful groupings of the data not present in the raw data source. These multidimensional groupings may likewise be performed before an end user accesses the data warehouse or executes a search. The multidimensional groupings may in embodiments furthermore be automatically analyzed using an inference engine to scan for, detect and record hidden, newly discovered relationships between attributes, data or other objects hosted in the data store. Those additional inferred groupings may according to embodiments of the invention then be incorporated back into the data mart or other data resource, permitting clinical managers and others to analyze past trends and model future events based on those identified correlations. According to embodiments of the invention in one regard, the analytics available to the end user may therefore be more powerful and flexible because they can encompass a greater range of possible groupings and queries. Queries and reports may be made more efficient because actual, inferred or potential relationships between data and data attributes may be pre-grouped and stored.

BRIEF DESCRIPTION OF THE DRAWINGS

The invention will be described with reference to the accompanying drawings, in which like numbers reference like elements.

DETAILED DESCRIPTION OF EMBODIMENTS

Figure 1:
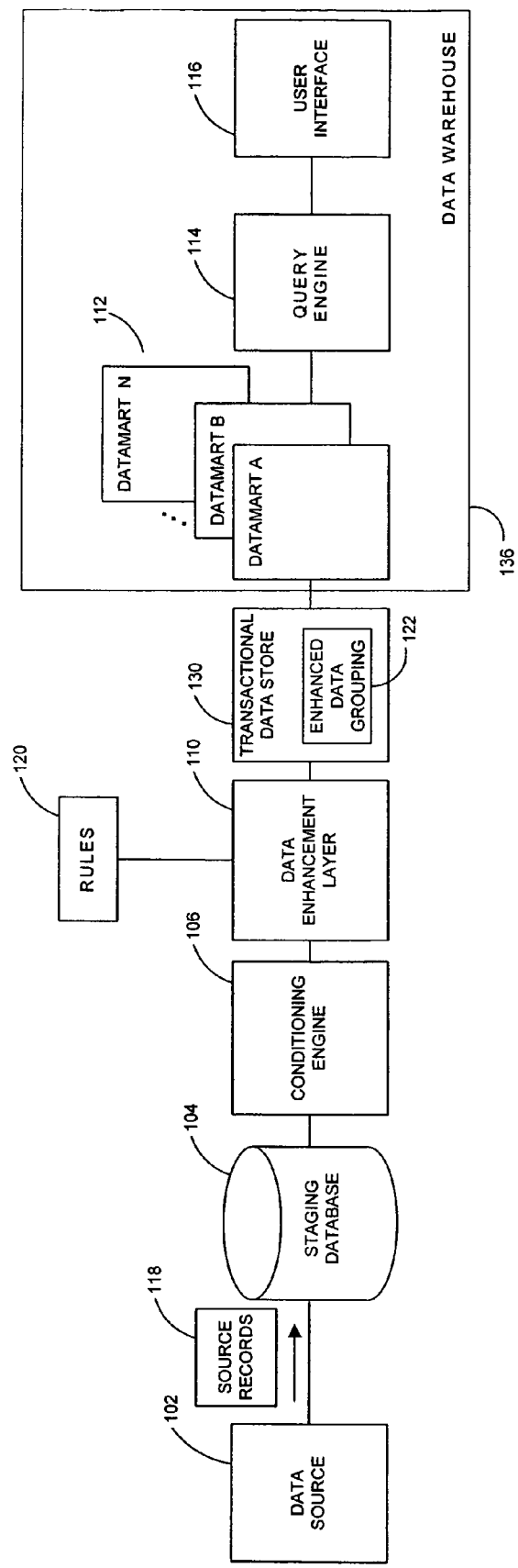
FIG. 1 illustrates an overall network architecture in which embodiments of the invention may operate.

An illustrative environment in which an embodiment of the invention may operate is shown in FIG. 1, in which a data sources 102 may communicate clinical medical or other data via a data enhancement layer 110 and other networked components to a transactional data store 130 and ultimately to a searchable set of datamarts 112 for analytic processing. The data sources 102 may be or include a medical or other site or facility, such as a hospital, laboratory, university, a military, government or other installation which may capture and store clinical and other data regarding patients, diagnoses, treatments and other aspects or outcomes of medical tests and other medical or other encounters or events.

The data sources 102 may transmit one or more source records 118 containing that clinical or other information via a network connection, such as the Internet, local area network (LAN), virtual private network (VPN) or otherwise to a staging database 104, for intermediate storage or processing before being communicated further in the storage service chain. The data sources 102 may for instance transmit the source records 118 on a fixed or periodic basis, such as one time per day, week or month, or on a variable or episodic basis, such as when a given amount of data is accumulated, a clinical trial is completed or otherwise.

Figure 2:
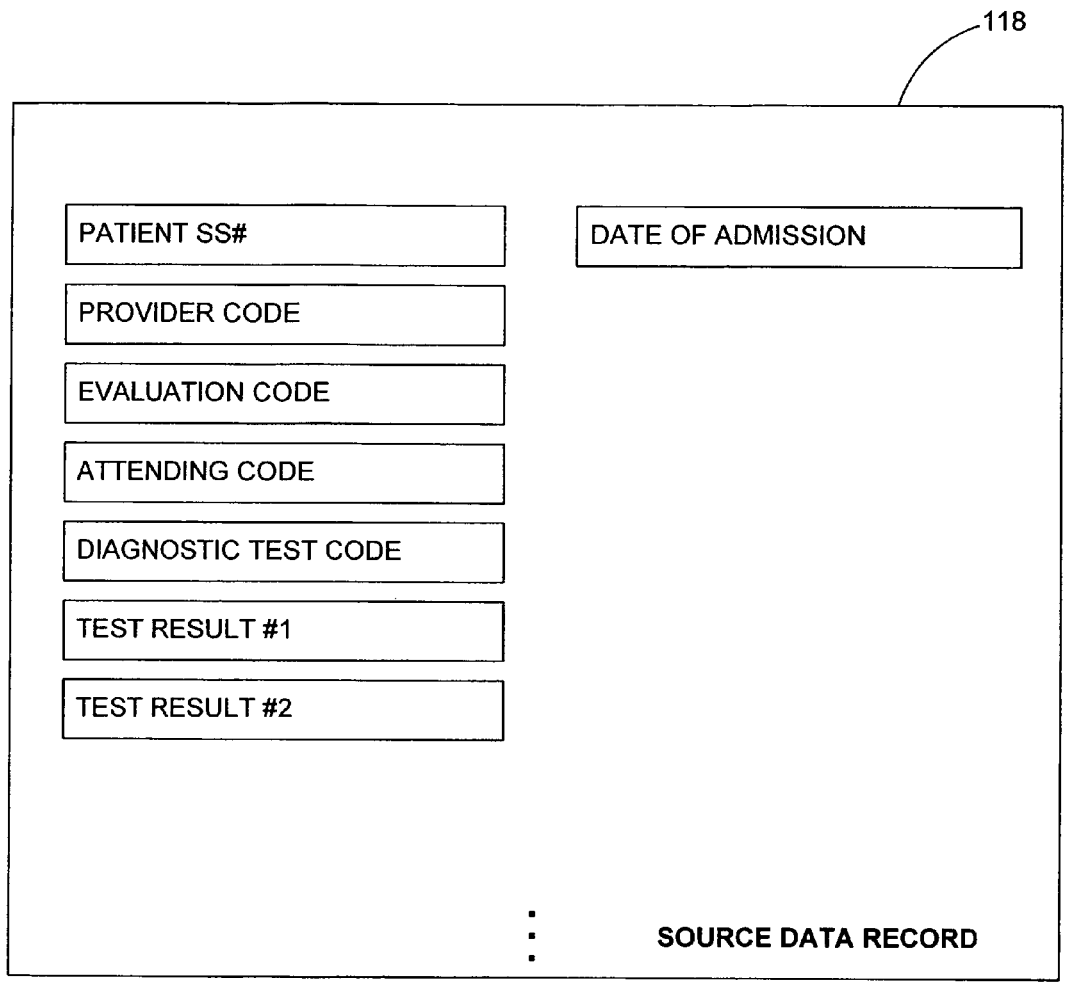
FIG. 2 illustrates an example source record, of a type which may be processed according to embodiments of the invention.

FIG. 2 illustrates one example format of one or more source records 118, in which incident, encounter or other data such as patient identifying information, doctor or other provider identifiers, date fields, diagnostic codes, test results fields and other information may be recorded. In embodiments, source records 118 may also be or include compound records, records which contain links to other records, or other content, formats or functionality.

The staging database 104 may receive the source records 118 and assemble and temporarily or permanently store that data for further transmission and processing. In embodiments staging database 104 may prepare the set of source records 118 for physical storage or logical formatting necessary for downstream warehousing or analytics. As illustrated, according to embodiments of the invention staging database 104 may communicate the source records 118 to a conditioning engine 106 for those purposes. Conditioning engine 106 may be or include, for instance, a server which parses the source records 118 to conform to OLAP or other standards.

Once any conditioning has been carried out, the source records 118 may be communicated to the data enhancement layer 110 for further processing before committing the source records 118 to permanent or other storage. According to embodiments of the invention in one regard, the data enhancement layer 110 may be or include a server with associated electronic, hard or optical disk storage and other computing, storage or network resources configured or programmed to manipulate source data records, identify or resolve relationships between data components, and store resulting multidimensional groupings to datamarts or elsewhere for analytic processing and other purposes.

More specifically, according to embodiments of the invention the creation, maintenance and extensions of data relationships that are both hierarchical and multidimensional in nature may be supported and extended via data enhancement layer 110 and other components. According to embodiments of the invention, a set of canonical rules 120 may be used to detect and develop relationships between data or attributes of subject data. The rules 120 may for instance represent or include defined data pairings which tend to indicate a relationship of interest, such as a causal or correlated relationship. The resulting relationships detected or outputs generated using rules 120, which may not have been present in or specified by the original data sources 102, may then in turn be embedded into or used to build a resulting enhanced data grouping 122, which may be stored to a transactional data store 130 and ultimately made available for searching, modeling and other purposes by end users and others. Among other things, the pre-generation of enhanced data grouping 122 whose cubic or other representation may already include ordered rows, columns, layers or other structures which associate meaningful variables or sets of variables together may enhance to power and efficiency of end user analytics. According to the invention in one regard, the performance of query engines using SQL constructs may for example improve because computationally expensive "join", "group-by" or other operations may be unnecessary.

The dimensions, number of axes, layers or other characteristics of enhanced data grouping 122 may extend beyond the nominal dimensions of the source records 118, aggregations of those records or other raw or original data. The resulting enhanced data grouping 122 may also be specific to or dependent on the original source content, which can be further aggregated into larger identified groups to produce meaningful analytics. According to the invention in one regard, the enhanced data grouping 122 may in embodiments embed or reflect relationships developed between attributes of data, rather than strictly the data values themselves, making manipulation of rules 120 more efficient and storage of enhanced data grouping 122 more economical. It may be noted that the dimensions of enhanced data grouping 122 may in general be unconstrained or freely selected, but may be chosen or changed to conform to particular data models used.

Due to the open nature of grouping strategies according to the invention in one regard, at least three types of relationships can be detected in the data enhancement layer 110 using rules 120 and other resources. Those types include known, derived and inferred relationships. The data enhancement layer 110 and other platform components may for one measure known relationships between data elements, such as those embedded in the original data sources 102. According to the invention in another regard, ad hoc querying using a manual process may be secondly employed to derive relationships that are not currently recognized or measured, but which may be revealed after interrogating a data store. According to embodiments of the invention in one regard, analytic tools, platforms or management interfaces such as those described in the aforementioned co-pending U.S. patent application Ser. No. 10/720,086 filed Nov. 25, 2003 entitled "System and Method for Evidence-Based Modeling of Clinical Operations" and in the aforementioned co-pending U.S. patent application Ser. No. 10/834,229 entitled "System and Method for Management Interface for Clinical Environments" may for example be used to query, model or project trends such as clinical outcomes, regulatory compliance, cost variables and other scenarios, based on known or pre-identified relationships, or relationships derived from direct interrogation of enhanced data grouping 122 and other data stores and resources.

Figure 8:
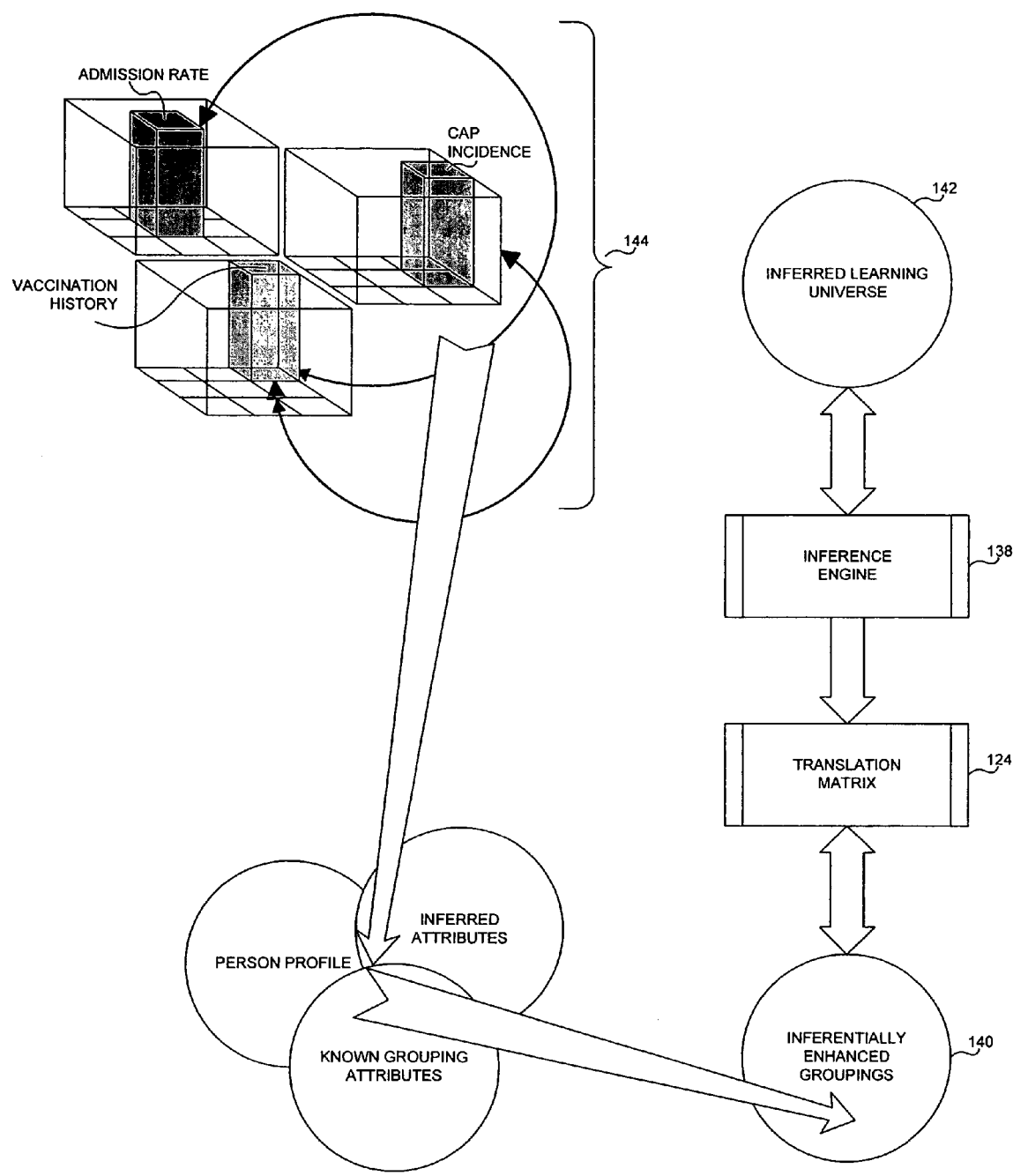
FIG. 8 illustrates an overall architecture in which a data store and related tools may operate to generate inferred data groupings, according to embodiments of the invention.

According to embodiments of the invention in a further regard, and as for example illustrated in FIG. 8, data mining and other analytics according to the invention in another regard can likewise be used to generate a third type or category of relationship, namely automatically detected groupings or inferred relationships 144 based on automatically generated and programmatically identified correlations within the enhanced data grouping 122, or other data.

That is, according to embodiments of the invention as for instance illustrated therein, an inference engine 138 may communicate with source clinical and other data generally located within inferred learning universe 142, which universe may be or include data sources 102, source facts 126, enhanced data grouping 122 itself or related data structures or stores, or other attributes, data or other information. In embodiments, the inference engine 138 may be, include or interface to, for example, a statistical engine such as the commercially available Statistica™ package available from StatSoft, Inc., the Mathematica™ package available from Wolfram Research, Inc., the SPSS™ package available from SPSS Inc., or other packages or platforms. In embodiments, the inference engine 138 may likewise be, include or interface to a Bayesian-type inference engine or other self-learning network such as a neural network, a state vector machine (SVM), or other statistical or logical engine, application or resource.

In embodiments as shown, the inference engine 138 may access the inferred learning universe 142 to detect inferred relationships 144, which relationships may be previously unidentified or undetected within enhanced data grouping 122 or other data structures. For instance as shown, the inference engine 138 may run statistical or inferential reports against the attributes, data or other information in inferred learning universe 142 to determine whether any two, three or more attributes, data or other pieces of information demonstrate a greater than random correlation or association with each other. For instance, the inference engine 138 may access a variable defined as "Admission Rate" grouped or hosted in one structure, an attribute or variable defined as "Vaccination History" grouped or hosted in another structure and an attribute or variable defined as "Community Acquired Pneumonia (CAP) Incidence" grouped or hosted in another structure, and may generate a statistical or inferential measure on the relatedness, association or correlation of those objects, for instance represented by a parametric or nonparametric correlation coefficient, mutual information, covariance, deviation, rank or other calculated tests, results or relationships.

If for example the Admission Rate, Vaccination History and CAP Incidence attributes or variables demonstrate, for instance, a correlation measure of 0.8 (on a scale of −1 to 1), it may be inferred that changes in for instance Vaccination History affect Admission Rate and CAP Incidence, in some greater than random fashion. Inference engine 138 may detect and substantiate one or more of these or other types of inferred relationships 144 within inferred learning universe 142, for instance generating correlation or other outputs based on ensembles of two or more attributes, data or other information. For instance those ensembles may be analyzed using partial or exhaustive reports or analytics run on any two, three or more attributes, data or other information available in inferred learning universe 142. The choice of attributes, data or other information may in embodiments be randomly chosen or rotated, or otherwise selected. According to embodiments of the invention in another regard, inferred relationships 144 may be generated in connection with or derived from clinical trial or related research activity, in which, for example, the administration of a new pharmaceutical product is being tested in a patient population. In trial applications of that and other types, the patterns or relationships between the drug or pharmaceutical, the dosing, potential adverse effects or other variables may not be known or identified beforehand. In those applications and others, use of tools and techniques according to the invention to discern and isolate inferred relationships 144 in those uncertain conditions may be advantageous.

Following identification and substantiation of any one or more inferred relationships 144, particular detected relationships may pass through translation matrix 124 for delivery to the overall data mart or data store, to be incorporated within inferentially enhanced groupings 140. Inferentially enhanced groupings 140 may in embodiments form a superset of, be added to or in cases be separately stored from enhanced data grouping 122. The inferentially enhanced groupings 140 may then become incorporated in the analytic, predictive and other tools and operations which operate in or on the overall set of datamarts 112 or other facility, to permit administrators and others to analyze and project costs, outcomes, trends and other scenarios and models of interest, using those further identified correlations.

Thus according to embodiments, the inferentially enhanced groupings 140 may be incorporated in the set of datamarts 112 or other data store or warehouse environment to populate solution set scenarios supporting analysis based on inferred, forecast, hidden or other relationships. Inferred groups may, consequently, be automatically identified and created based on statistical, logical or inferential qualification or quantification. This facility may permit an end user to pinpoint correlations between events, such as for example drugs, dosings, procedures, timing of events etc. and outcomes such as extended length of stays, mortality, complications, infections or others that the end user or facility was not aware, had not predicted or which would not be evident on first inspection of the information, or whose complexity or scale might be too great for human detection or estimation.

As noted, a conventional approach to data warehousing is to retain the relationships of the data sources 102, and if any new relationships are needed, to create those relationships in that source and then extract the relationships into the warehouse facility. If the data groupings necessary for analytics can not be accommodated in the original data sources 102, the general conventional approach is to then create them at a back-end or presentation layer through a querying and reporting tool. Due to the complexities of some large-scale data stores, and of health care data in particular, compared for instance to data warehouses in retail, banking or manufacturing industries, these approaches may not accommodate the analytic demands of end users.

Addressing these and other disadvantages of a source-driven approach, according to the invention in one regard the data sources 102 again may communicate the source records 118 to the data enhancement layer 110 and transactional data store 130 to generate data enhancements including extended or derived groupings not present in the original source records 118. According to the invention in one respect, the data enhancement layer 110 and transactional data store 130 may use the attributes of the original data from source records 118 themselves to define extended dimensions, develop or apply rules 120, grouping configurations and additional element attributes to generate enhanced data grouping 122.

Figure 3:
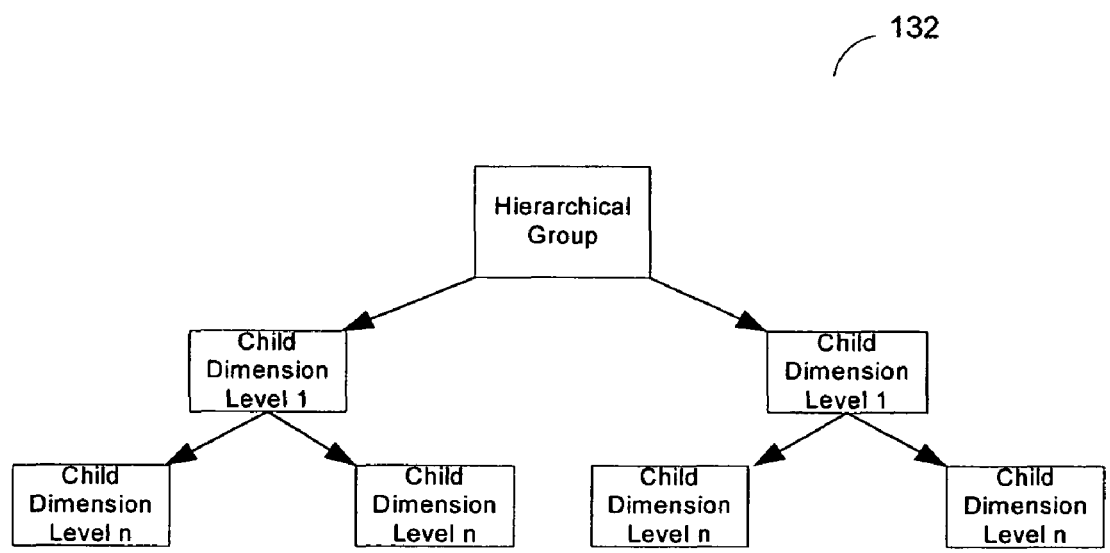
FIG. 3 illustrates a logical diagram of a hierarchical grouping, which may be processed according to embodiments of the invention.

There are at least two types of potential data groupings for extension and other purposes, namely hierarchical and multidimensional. As illustrated in FIG. 3, a hierarchical grouping 132 is a logical structure that uses ordered levels as a means of organizing data. This logical structure is made up of levels, parent and children. A level is a position in a hierarchy, a parent is a value at the level above a given value in a hierarchy and a child is the value at the level under a given value in a hierarchy. This grouping scheme may be used to define a data grouping or aggregation in a hierarchical structure, although it may be noted that in cases a grouping may be generated based on one or more dimension attributes that do not have an ordered relationship. For example, a general ledger account of "Net Income" may be made up of accounts that are allocated to net income. In order to accommodate this variety of data, users may need to be able to specify which sub-accounts "roll-up" into the main account. Thus, a general ledger summary account (e.g. total labor expense) would need to be a hierarchical account that is the parent to a series of children sub-accounts at different levels. This logical structure may then also be required to specify common costing allocation processes. According to the invention in one regard, data sources 102 may be or include source records 118 which are organized in a hierarchical fashion.

Figure 4:
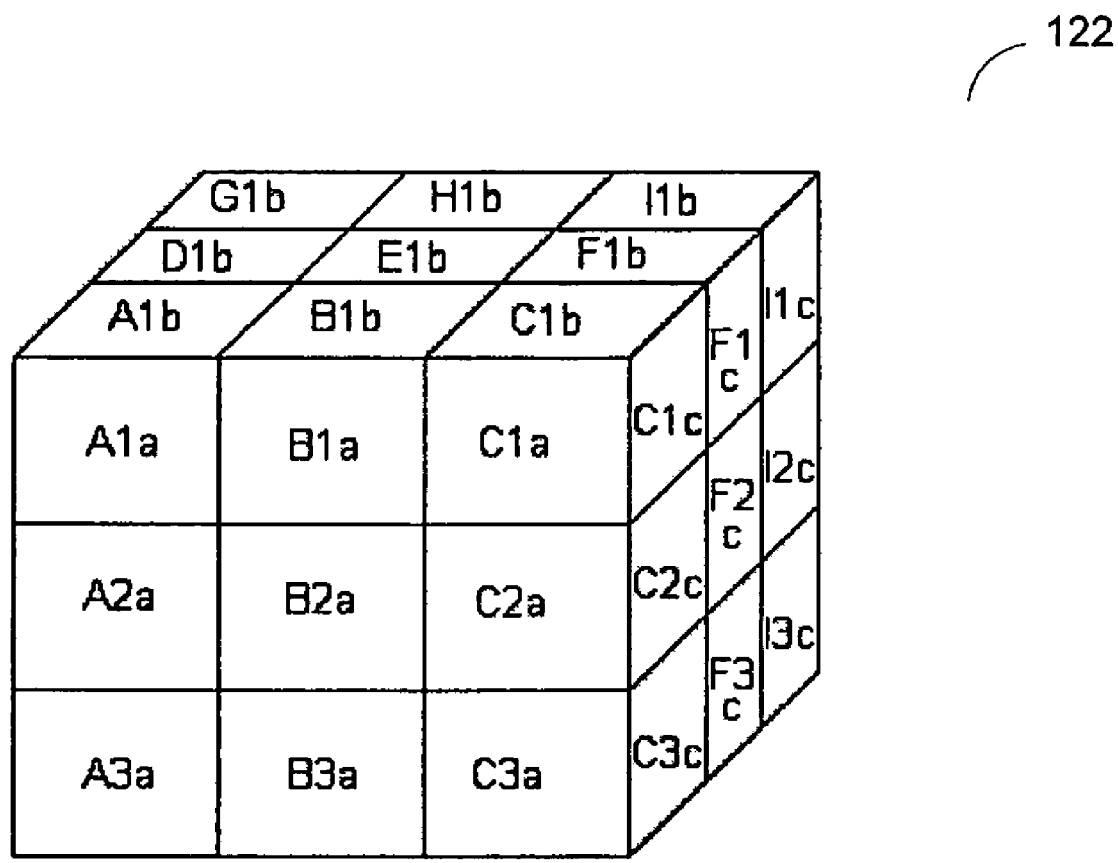
FIG. 4 illustrates an example enhanced multidimensional data grouping, which may be generated according to embodiments of the invention.

As schematically illustrated in FIG. 4, enhanced data grouping 122 may among other things rely upon a further type of grouping, multidimensional grouping, in a separate logical structure which may be used to create or extend the new dimensions that are based on the values of a series of dimensions or other attributes. Multidimensional groupings may be arranged, for example, as a cube in 3-space in which individual columns, rows and layers reflect different attributes, variables or other quantities or objects. For example, the multidimensional group for the service line of "Cardiology" could be determined as the patients that have the encounter type of inpatient, age greater than 18, diagnosis codes 390.0-459.9, physician specialty of cardiologist and a particular nurse unit. This group may then be used to analyze different aggregations for this series of dimensions. According to the invention in another regard, the groupings generated in data enhancement layer 110 may facilitate the analysis of the entire group (represented by the whole cube), one side (A1a-C3a), one column (A1a-A3a), one row (A1a-C1a), one attribute (A1) or other aspects of the enhanced data grouping 122. An attribute can be thought of as an object of reference, either a dimension or fact (modality of reference). Additionally, multidimensional groupings in general and the enhanced data groupings 122 generated according to the invention in particular may have the ability to establish cross-relationships.

That is, dimensions grouped as members of one group can be grouped as members of another. For example, a physician could be grouped to the both the specialty of "Oncologist" and "Internal Medicine". The driving variable which determines which specialty the data is grouped to are the values that make up that multidimensional grouping. In other words, the "Oncologist" specialty for this physician may have a different series of values than the "Internal Medicine" specialty. As patient activity occurs for this physician, the combination of the values may then dictate which group may be populated.

By having the ability to accommodate both hierarchical and multidimensional data, embodiments of the invention may support analytics that utilize both types of groups. For example, an end user could use the multidimensional group of "Cardiology" and the hierarchical group of "Net Income" to evaluate the net income that was generated by the cardiology service line, using a single report or analytic tool.

Figure 5:
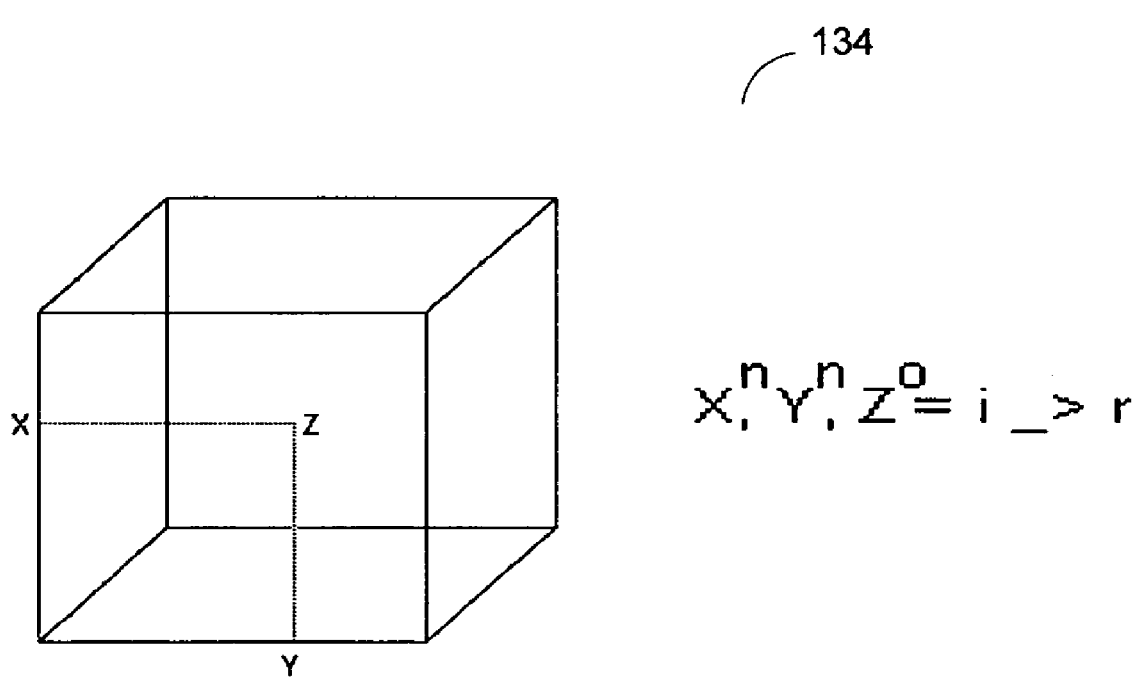
FIG. 5 illustrates a dimensional diagram of data organization, according to embodiments of the invention.

To accomplish these and other results, according to the invention the data enhancement layer 110 may first acquire and represent the dimensional attributes from one or more data sources 102. As illustrated in FIG. 5, once the source records 118 or other original data are acquired, relationships may be defined in or using a schematic physical structure 134 through the application of the following equation:

$$X^n, Y^n, Z^0 = i\_>r$$

where
 X, Y=Dimension attributes
 Z=Fact reference to transactional activity
 i_>r=Intersection functionally determines result set.

Figure 6:
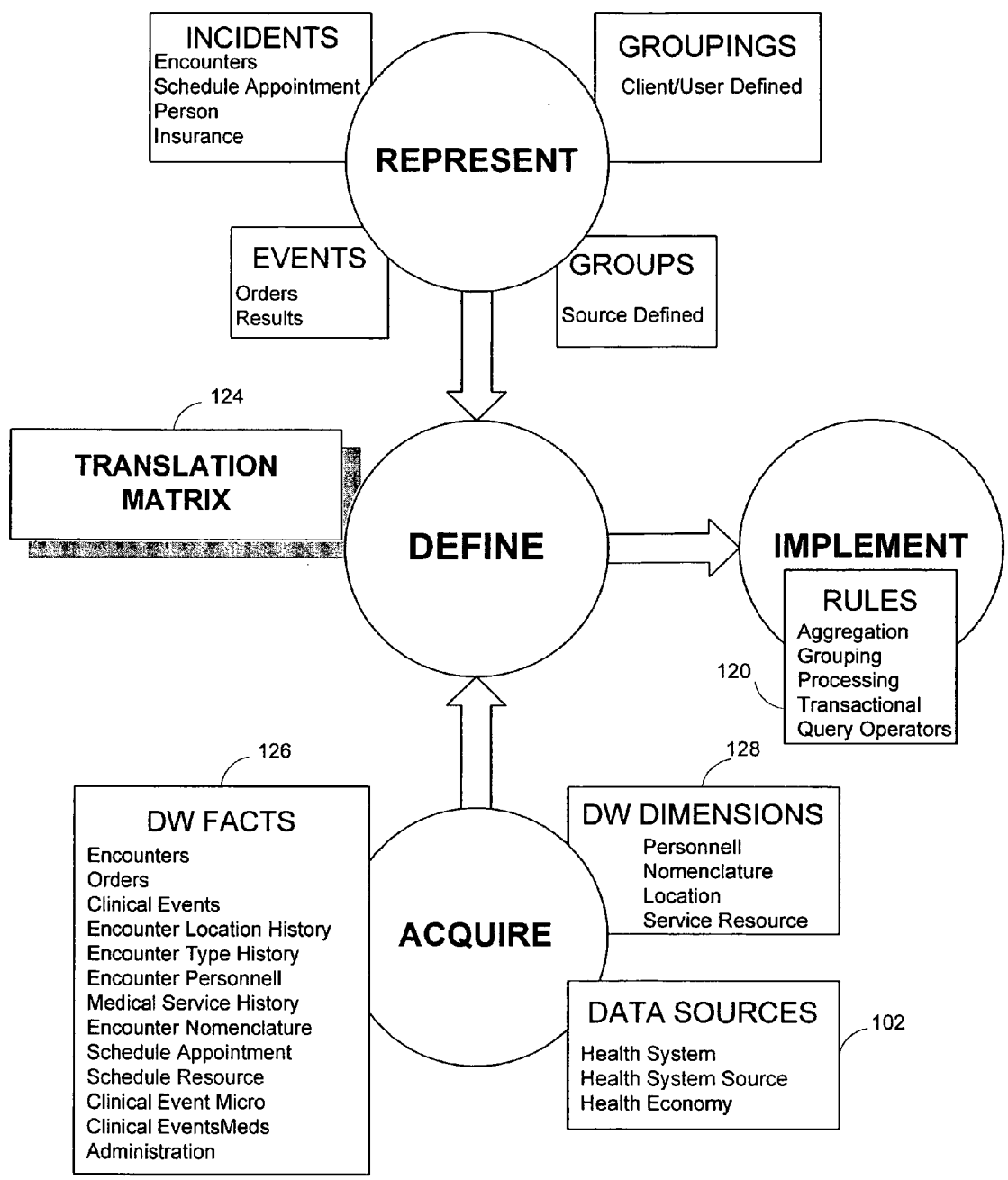
FIG. 6 illustrates a diagram of the generation of physical storage structures, according to embodiments of the invention.

FIG. 6 illustrates a diagram of physical structures embedded or used to organize or store source records 118 at various stages of processing according to embodiments of the invention, once those record are acquired. As illustrated, data may be collected from one or more data sources 102, such as a health system or company or various other clinical or other facilities or sources. The source records 118 delivered by data sources 102 may contain diverse fields or components, including source facts 126 such as encounters, orders, clinical events and other personal, medical, administrative and other data. The data delivered by data source may likewise include or have associated with it dimensions 128, defining or related to multidimensional cubic or other representations of the data. The source records 118 along with source-defined groupings, source facts 126, dimensions 128 and other data may be assimilated into the process of generating rules 120 by which the aggregate of source data records may be extended by multidimensional groupings, for instance to associate clinically related variables in the same column, row or other space.

As illustrated in that figure, the generation of rules 120 may be performed or aided by a translation matrix 124, which may be independent from, augment or be part or data enhancement layer 110. In embodiments the rules 120 may be generated by processing the results of prior analytics, by predefined groupings, by automated detection of event or other correlations, or by other techniques. It may be noted that physical structures such as hard disk partitioning of large data arrays may mirror the organization of enhanced data grouping 122 or other components or aspects of data stored to the set of datamarts 112, or other resources.

After the enhanced data grouping 122 has been defined in a physical storage structure or otherwise, that grouping may be implemented into the transactional data store 130 and ultimately delivered to an appropriate one or more of the set of datamarts 112, for example using further rule translations and thus making the enhanced data grouping 122 transparently available to the end user.

The following is an example of variables which may be used to generate an enhanced data grouping 122 for the service line of "Cardiology", according to embodiments of the invention:

| | |
|---|---|
| X = | DW_Encounters E |
| | DW_Encounters_Nomenclature N |
| Y = | E.Encounter Type - Inpatient |
| | E.Age > 18 |
| | E.Physician - Cardiologist |
| | N.Diagnosis Code 390.0-459.9 |
| Z = | # of Admits > 0 |
| i_>r = | Cardiology |

In order to accommodate this flexible approach to groupings which is not source-constrained, the data enhancement layer 110 and other components of the invention may manage and represent fact, dimension and attribute data within at least either a hierarchy or a multidimensional data strategy. In that strategy or implementation both a logical and physical representation of rules and data may be used. Embodiments of the invention may thus represent transactional data elements without the use of core activity data itself, but instead rely solely on the attributes of fact and dimensional data.

In this regard, the source records 118 and the constituent data may themselves define or be used to define dimensions, rules 120, grouping configurations, element attributes and other criteria used to generate enhanced data grouping 122. As illustrated for example in FIG. 3, the physical structure of the data may identify at least source data relationships, source data element relationships, source data attribute relationships, source data aggregation and source data consolidation, among other things.

According to the invention in another regard, the management of the mapping of results space to input space may be accomplished by applying "soft data" strategies known to persons skilled in the art. The so-called Soft Data Theorem for instance may be used to take advantage of the fact that dimensions have an inherent hierarchy of determinant data structures and variables, which can be exploited to assist in the generation of enhanced data groupings 122. This approach concentrates on representing data through selective attribute representations of reference data. The technique enables, among other things, the ability to manage multi-dimensional cross-relationships, to relate different levels of aggregation, to relate data at varying granularities, relate data at varying perspectives (cubes, either hyper or multi), density increases at higher consolidation levels and the ability to manage results space to input space for both system-defined and user-defined values.

The grouping strategies employed by the invention may provide logical aggregation through combining attributes of multiple dimensions 128 that define one group of fact records, as opposed to a physical aggregation that requires schema and foreknowledge of the required dimensions and facts from data sources 102 or otherwise. Among other advantages, this may simplify queries by allowing end users to group multiple conditions into a "super group", enhance query performance by reducing the number of SQL or other joins required, allow site-specific dimension groupings, and again enable a common grouping strategy for disparate sources of data.

As noted, the constructs under which data groupings are applied to generate enhanced data grouping 122 support normalized rules 120 of functional determination. At least three of rules 120 may be fundamental and represent existing data behavior that are determinate, possess normalized relationships and may be inherent to other derivatively-defined relationships. Those three rules among rules 120 are identified as:

TABLE 1

| | |
|---|---|
| Reflective Rule: | X contains Y, then X -> Y |
| Augmentation Rule: | {X->Y} implies XZ -> YZ |
| Transitive Rule: | {X->Y, Y->Z} implies X->Z |

Other types or classes of inference or other rules may be included within rules 120, including for example:

TABLE 2

Resolution: For all clauses C, D and variables A,
  (C v A) (*A v D)
    (C v D), in which C v D is said to be resolvent, A is a resolved atom.
Factoring: For all clauses C and variables A,
  (C v A v A)
    (C v A). referred to as C v A factor.

Other types or classes of rules may be used.

Further, inferred relationships 144 or other deduced or detected relationships may be hypothesized to have leverage where inferences would exist through possible approximation and differential substantiation. Additional insight into direction of vector(s) intersecting with opposing planes through fact activity supported through the following additional instances of rules within rules 120:

TABLE 3

| | |
|---|---|
| Projection Rule: | {X->YZ} implies X->Y |
| Union Rule: | {X->Y, X->Z} implies X->YZ |
| Pseudo-Transitive Rule: | {X->Y, WY->Z} implies WX->Z |

These and other rules 120 such as those in the following table represent object and data-related relationships supported within schema, structure and query definitions, such as those supported or required by SQL, OLAP or other data platforms.

TABLE 4

Base Relations: Physical SQL base tables. Otherwise known as the real relations. These real relations are defined by the physical data warehouse structure.
Views: The virtual relations. A named, derived relation. May also exist as logical layer. Views are defined at the database layer.
Snapshots: A real, not virtual, named derived relation showing the status of an entity at a point in time.
Query Results: The final output relation from a specified query. It may not be named and has no permanent existence. Results can be defined through solution sets or ad hoc query activity.
Temporary Relations: A nonpermanent named derived relation, either physical or virtual, that persists for indeterminate amount of time.

According to embodiments of the invention in another regard, additional requirements may arise due to differences that may exist between online transaction processing (OLTP) and OLAP implementations. Transforming OLTP data to an acceptably performing OLAP system may require a number of functionalities.

Those intermodal functionalities may include:

TABLE 5

Ability to Merge All Data related to specific items from multiple OLTP systems.
Ability to Resolve Differences in encoding between the different OLTP systems.
Ability to Match Common Data from disparate systems, even data with inconsistencies.
Ability to Convert Different Data types in each OLTP system to a single OLAP type.
Ability to Select Column Data in the OLTP system are not relevant to an OLAP system.
Ability to Absorb Input Data not strictly limited to centrally located OLTP systems.
Ability to Scrub Data - Address inconsistencies to modeled data and process structures.
Inconsistencies have to be addressed before data can be loaded into a warehouse for use.
Ability to represent Aggregate Data Relationships notwithstanding transaction details.
Ability to Optimize Aggregate Performances using "Modular Fact Granularities".
Ability to Organize Data in Cubes—Since dimensional attributes are stored in structures designed to represent actual reference data, which already exist in multi-dimensional cube organizations to support analytics, transformation may be achieved through rules structures.
Ability to represent Meta Data Objects in OLTP databases, cubes in data warehouses and datamarts which applications use to reference the various pieces of data.

According to the invention in a further regard, formulated assumptions for aspects of operation of the invention include that facts can only exist at one level of granularity, that the intersection points at any resulting row or rows on fact, and that hierarchical groupings are two-dimensional in nature. Data movement outside the data enhancement layer 110 and other portions of the supporting platform may support a push-pull relationship between the transactional and outcomes measurement layer. Extractions from source-specific to outcomes measurement may bypass the transactional layer but may be ultimately required to feed back to support user-defined groupings. In terms of data movement of source records 118 and other data objects received or generated by the invention, functional requirements for data transport include a channel or facility for pulling data from data sources 102 and set of datamarts 112, and push data to the transactional data store 130 and other repositories.

In terms of schema for ancillary physical structures according to embodiments of the invention, the translation matrix 124 may define or process at least the following functions or combinations:

TABLE 6

Dimension and fact combinations.
Dimension and fact to source.
Dimension and fact to incident types.
Dimension and fact to incident with factors to events.
Groups to represent source-specific groups.
Groupings to represent warehouse-derived groupings - may include groups.
Ability to be represented as outcome measurement.

Once the source records 118 have been processed according to rules 120 or other paradigms and the enhanced data grouping 122 has been generated and stored to an appropriate one or more of the set of datamarts 112, according to embodiments of the invention a systems administrator, researcher or other end user may run queries against the set of datamarts 112 via query engine 114. The end user may execute those actions for instance using a user interface 116 such as an OLAP, SQL or other query or user interface, for instance using a graphical user interface interfacing to query engine 114. As an example, the end user may run a report against one or more of the set of datamarts 112 using query engine 114 and user interface 116 to formulate a query against hospital inpatient records to ask, for instance: How many patients admitted to the hospital last year exhibited blood glucose levels above 200, along with positive detection of A1C hemoglobins?

That query might serve to detect persons having diabetes or at risk for diabetes, whether or not they were admitted or treated for that condition. Similarly, as another example a hospital administrator or other end user might execute a query against one or more of the set of datamarts 112 to determine average patient reimbursements or billings for all cardiac or oncology patients admitted in the last month. Other queries or reports are possible. According to embodiments of the invention in another regard, the complex of the set of datamarts 112, query engine 114 and user interface 116 as well as other elements or resources may together be referred to as data warehouse 136, although implementations may vary.

Figure 7:
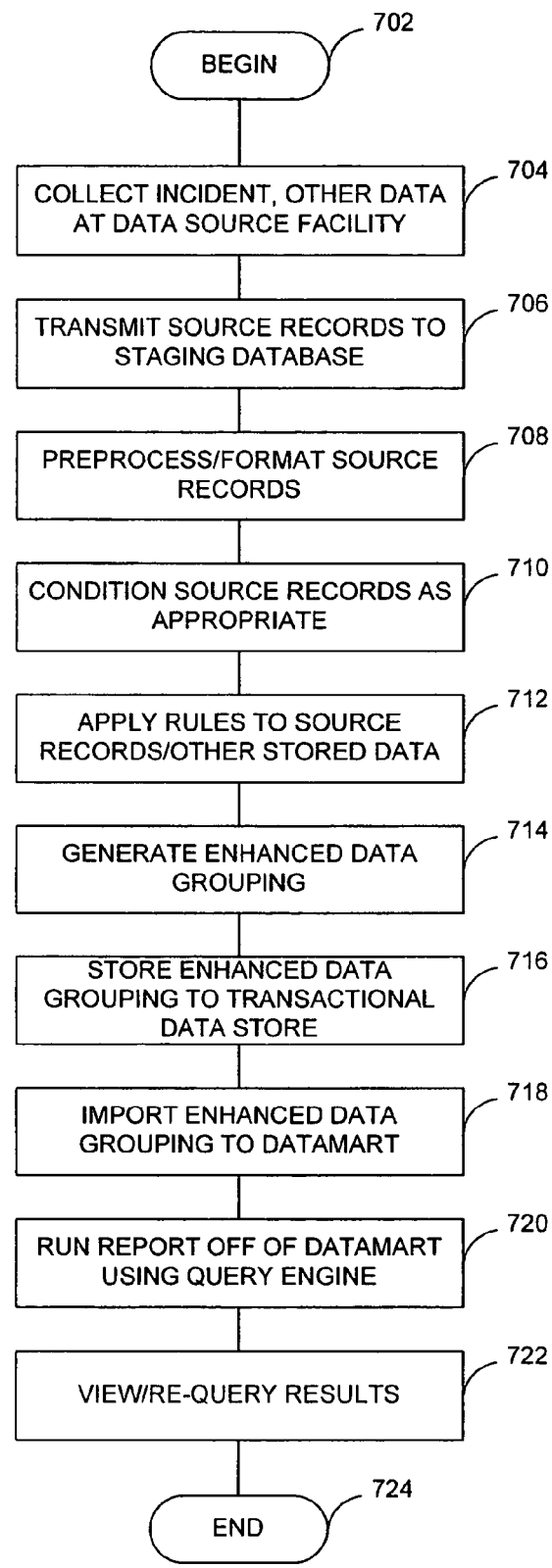
FIG. 7 illustrates a flowchart of overall processing according, to embodiments of the invention.

Overall data processing according to an embodiment of the invention is illustrated in FIG. 7. In step 702, processing may begin. In step 704, patient incident or other data may be collected at a data sources 102, such as a hospital, laboratory or other site or facility. In step 706, the resulting source records 118 may be transmitted to the staging database 104 or other intermediate destination. In step 708, the source records 118 may be preprocessed, formatted or otherwise treated to permit or enhance downstream communication or processing. In step 710, the source records 118 may be conditioned by conditioning engine 106, for instance for storage in OLAP or other storage platforms.

In step 712, the data enhancement layer 110 may apply rules 120 to source records 118 or aggregations of source records 118 and other information. In step 714, data enhancement layer 110 may generate an enhanced data grouping 122. In step 716, the enhanced data grouping 122 may be stored to transactional data store 130 or elsewhere. In step 718, the enhanced data grouping 122 and other data may be imported to the set of datamarts 112. In step 720, a systems administrator, analyst or other end user may run a report off of one or more of the set of datamarts 112, for instance to analyze disease, drug efficacy, therapeutic, demographic or other trends. In step 722, the results of any report or query may be viewed and re-queried if desired. In step 724, processing may repeat, return to a prior point or end.

The foregoing description of the invention is illustrative, and modifications in configuration and implementation will occur to persons skilled in the art. For instance, while the invention has generally been described in terms of a single data enhancement layer 110, in embodiments multiple enhancement layers may be employed. Likewise, while in embodiments the invention has generally been described or illustrated as involving the detection, identification or generation of inferred relationships 144, inferentially enhanced groupings 140 and related information which may be multi-dimensional in nature, in embodiments the inferred relationships 144, inferentially enhanced groupings 140 and other data structures may be dimensional, meaning in one respect created by an array of attributes of a single dimension, as well. Similarly while the invention has generally been illustrated in terms of one data sources 102 communicating data to the data enhancement layer 110 and other system stages, in embodiments multiple data sources may communicate a variety of source records and other information to the data enhancement layer 110 and other components.

Similarly, while the invention has in embodiments been described as processing and enhancing medical or clinical data, in embodiments data of other types or categories may be received and treated. The scope of the invention is accordingly intended to be limited only by the following claims.

ELEMENTS LISTS

Data sources 102
Staging database 104
Conditioning engine 106
Attribute relationships 108
Data enhancement layer 110
Set of datamarts 112
Query engine 114
User interface 116
Source records 118
Rules 120
Enhanced data grouping 122
Translation matrix 124
Source facts 126
Dimensions 128
Transactional data store 130
Hierarchical grouping 132
Physical structure 134
Data warehouse 136
Inference engine 138
Inferentially enhanced groupings 140
Inferred learning universe 142
Inferred relationships 144

What is claimed is:

1. A system for generating an inferred data grouping, comprising:
    an input interface receiving clinically relevant source data from a first data source and clinically relevant source data from a second data source, wherein each of the first data source and the second data source comprises a healthcare provider, a hospital, an insurer, a laboratory, or a medical facility;
    an inference engine, the inference engine
        communicating with the input interface to access the clinically relevant source data,
        automatically detecting an inferred clinical relationship between at least one attribute or data in the clinically relevant source data from the first data source and at least one attribute or data in the clinically relevant source data from the second data source being separate from the first data source comprising the healthcare provider, the hospital, the insurer, the laboratory, or the medical facility, wherein the inferred clinical relationship is automatically detected using an inference measure to detect and substantiate the inferred clinical relationship,
        generating an inferred data grouping in accordance with the detected inferred clinical relationship, and
        combining the inferred data grouping with an existing clinical data grouping to generate an inferentially enhanced data grouping that is used to analyze past healthcare-related trends and model future healthcare-related events to project a healthcare-related cost, outcome, trend, or interest; and
    a query engine, the query engine
        receiving a user query,
        in response to receiving the user query, utilizing the inferentially enhanced data grouping to analyze one or more healthcare-related trends, and
        providing a user with output based on the one or more healthcare-related trends.

2. A system according to claim 1, wherein the clinically relevant source data from the first data source comprises data generated by at least one of a health care provider, a hospital, an insurer and a laboratory.

3. A system according to claim 1, wherein the inference measure comprises a correlation measure between the at least one attribute or data in the clinically relevant source data from the first data source and at least one attribute or data in the clinically relevant source data from the second data source.

4. A system according to claim 1, wherein the inferred data grouping comprises a dimensional or multidimensional data grouping.

5. A system according to claim 4, wherein the dimensional or multidimensional data grouping is combined with the existing clinical data grouping to generate an inferentially enhanced dimensional or multidimensional data grouping.

6. A system according to claim 1, wherein the inference engine stores the inferred data grouping to a datamart.

7. A system according to claim 6, wherein the datamart is configured to receive queries.

8. A system according to claim 7, wherein the queries comprise standard query language queries.

9. A system according to claim 7, wherein the queries comprise at least one of analytic and predictive processing applied to the inferred data groupings.

10. A system according to claim 9, wherein the inferred data groupings are associated with clinical trial activity.

11. A computer-implemented method for generating an inferred data grouping, comprising:
    receiving clinically relevant source data from a first data source and clinically relevant source data from a second data source, wherein each of the first data source and the second data source comprises a health care provider, a hospital, an insurer, a laboratory, or a medical facility;
    automatically detecting an inferred clinical relationship between at least one attribute or data in the clinically relevant source data from the first data source and at least one attribute or data in the clinically relevant source data from the second data source being separate from the first data source comprising the healthcare provider, the hospital, the insurer, the laboratory, or the medical facility, wherein the inferred clinical relationship is automatically detected using an inference measure to detect and substantiate the inferred clinical relationship;
    generating, via a data enhancement layer, an inferred data grouping in accordance with the detected inferred clinical relationship;
    combining the inferred data grouping with an existing clinical data grouping to generate an inferentially enhanced data grouping that is used to analyze past healthcare-related trends and model future healthcare-related events to project a healthcare-related cost, outcome, trend, or interest;
    in response to receiving a user query, utilizing the inferentially enhanced data grouping to analyze one or more healthcare-related trends; and
    providing a user with output based on the one or more healthcare-related trends.

12. A method according to claim 11, wherein the clinically relevant source data from the first data source comprises data generated by at least one of a health care provider, a hospital, an insurer and a laboratory.

13. A method according to claim 11, wherein the inference measure comprises a correlation measure between the at least one attribute or data in the clinically relevant source data from the first data source and at least one attribute or data in the clinically relevant source data from the second data source.

14. A method according to claim 11, wherein the inferred data grouping comprises a dimensional or multidimensional data grouping.

15. A method according to claim 14, wherein the dimensional or multidimensional data grouping is combined with the existing clinical data grouping to generate an inferentially enhanced dimensional or multidimensional data grouping.

16. A method according to claim 11, further comprising storing the inferred data grouping to a datamart.

17. A method according to claim 16, wherein the datamart is configured to receive queries.

18. A method according to claim 17, wherein the queries comprise standard query language queries.

19. A method according to claim 17, further comprising applying at least one of analytic and predictive processing to the inferred data groupings based on the queries.

20. A method according to claim 19, wherein the inferred data groupings are associated with clinical trial activity.

21. A method according to claim 17, wherein the queries comprise standard query language queries.

22. A method according to claim 17, wherein the method further comprises applying at least one of analytic and predictive processing to the inferred data groupings based on the queries.

23. A method according to claim 22, wherein the inferred data groupings are associated with clinical trial activity.

24. A method for generating an inferred data grouping, the method comprising:
    receiving clinically relevant source data from a first data source and clinically relevant source data from a second data source, wherein each of the first data source and the second data source comprises a health care provider, a hospital, an insurer, a laboratory, or a medical facility;
    automatically detecting an inferred clinical relationship between at least one attribute or data in the clinically relevant source data from the first data source and at least one attribute or data in the clinically relevant source data from the second data source being separate from the first data source comprising the healthcare provider, the hospital, the insurer, the laboratory, or the medical facility, wherein the inferred clinical relationship is automatically detected using an inference measure to detect and substantiate the inferred clinical relationship;
    generating, via a data enhancement layer, an inferred data grouping in accordance with the detected inferred clinical relationship;
    combining the inferred data grouping with an existing clinical data grouping to generate an inferentially enhanced data grouping that is used to analyze past healthcare-related trends and model future healthcare-related events to project a healthcare-related cost, outcome, trend, or interest;
    in response to receiving a user query, utilizing the inferentially enhanced data grouping to analyze one or more healthcare-related trends; and
    providing a user with output based on the one or more healthcare-related trends.

25. A method according to claim 24, wherein the clinically relevant source data from the first data source comprises data generated by at least one of a health care provider, a hospital, an insurer and a laboratory.

26. A method according to claim 24, wherein the inference measure comprises a correlation measure between the at least one attribute or data in the clinically relevant source data from the first data source and at least one attribute or data from the second data source.

27. A method according to claim 24, wherein the inferred data grouping comprises a dimensional or multidimensional data grouping.

28. A method according to claim 27, wherein the dimensional or multidimensional data grouping is combined with the existing clinical data grouping to generate an inferentially enhanced dimensional or multidimensional data grouping.

29. A method according to claim 24, wherein the method further comprises storing the inferred data grouping to a datamart.

30. A method according to claim 29, wherein the datamart is configured to receive queries.

31. A method for generating an output based on an inferred data grouping, the method comprising:
    receiving clinically relevant source data from a first data source and clinically relevant source data from a second data source, wherein each of the first data source and the second data source comprises a health care provider, a hospital, an insurer, a laboratory, or a medical facility;
    automatically detecting an inferred clinical relationship between at least one attribute or data in the clinically relevant source data from the first data source and at least one attribute or data in the clinically relevant source data from the second data source being separate from the first data source comprising the healthcare provider, the hospital, the insurer, the laboratory, or the medical facility, wherein the inferred clinical relationship is automatically detected using an inference measure to detect and substantiate the inferred clinical relationship, the inference measure comprising a statistical correlation measure between the at least one attribute or data in the clinically relevant source data from the first data source and the at least one attribute or data in the clinically relevant source data from the second data source generating, via a data enhancement layer, an inferred data grouping in accordance with the detected inferred clinical relationship, the inferred data grouping comprising a hierarchical or multidimensional data grouping;
    combining the inferred data grouping with an existing clinical data grouping to generate an inferentially enhanced hierarchical or multidimensional data grouping, wherein the inferentially enhanced data grouping is used to analyze past healthcare-related trends and model future healthcare-related events, wherein one or more users can project a healthcare-related cost, outcome, trend, or interest;
    in response to receiving a user query, utilizing the inferentially enhanced data grouping to model future healthcare-related events pertaining to disease, drug efficacy, therapeutic, or demographic trends; and
    providing a user with output based on the modeling of future healthcare-related events.

32. A method according to claim 31, wherein the clinically relevant source data from the first data source comprises data generated by at least one of a health care provider, a hospital, an insurer and a laboratory.

* * * * *